US007759466B2

(12) United States Patent
Skerritt

(10) Patent No.: US 7,759,466 B2
(45) Date of Patent: Jul. 20, 2010

(54) MONOCLONAL ANTIBODIES TO ALPHA-AMYLASE

(75) Inventor: John Howard Skerritt, Cook (AU)

(73) Assignee: Bayer CropScience AG, Monheim (DE)

( * ) Notice: Subject to any disclaimer, the term of this patent is extended or adjusted under 35 U.S.C. 154(b) by 534 days.

(21) Appl. No.: 11/421,712

(22) Filed: Jun. 1, 2006

(65) Prior Publication Data

US 2007/0037233 A1 Feb. 15, 2007

Related U.S. Application Data

(62) Division of application No. 09/830,876, filed as application No. PCT/AU99/00995 on Nov. 11, 1999, now Pat. No. 7,074,579.

(30) Foreign Application Priority Data

Nov. 11, 1998 (AU) .................................. PP7058

(51) Int. Cl.
*C12P 21/08* (2006.01)
(52) U.S. Cl. ............................. 530/388.26; 530/388.1; 530/866; 436/547; 436/548; 436/808
(58) Field of Classification Search ....................... None
See application file for complete search history.

(56) References Cited

U.S. PATENT DOCUMENTS 4,863,728 A * 9/1989 Gerber et al. ............. 424/146.1
6,031,155 A * 2/2000 Cameron-Mills et al. ... 800/284

FOREIGN PATENT DOCUMENTS

AU         758659 B2    4/1999

OTHER PUBLICATIONS

Khursheed et al. The Journal of Biological Chemistry. vol. 263, No. 35. pp. 18953-18960. Dec. 15, 1988.*
Kohler. Science. 233 (4770):1281-1286. 1986.*
SCORE Results. 2008.*
"Annual Wheat Newsletter—HTML Version," vol. 44, Jul. 20, 1998, [online] Retrieved from the Internet<URL:http://wheat.pw.usda-gov/ggpages/AWN/44/1exttiles/AUSTRAL>.
Chandler, P.M. et al., "The Effects of Gibberellic Acid and Abscisic Acid on α-Amylase mRNA Levels in Barley Aleurone Layers Studies Using an α-Amylase cDNA Clone," Plant Molecular Biology, 1984, pp. 407-418, vol. 3.
"Determination of Falling Number," Physiochemical Tests, AACC Method 56-81B, Nov. 2, 1972, pp. 1-4.
"Evaluation of WheatRite™ Test Kits for Sprouted Grain," VICAM—WheatRite Evaluation, Jan. 18, 2000, pp. 1-7.
Gibson, C.E. et al., "The Rapid Detection of Barley Malt Quality Enzymes Using an Enzyme-Linked Immunosorbent Assay (ELISA)," Proceedings of the 44th Australian Cereal Chemistry Conference, Royal Australian Chemical Institute, Melbourne, 44 (1994) 174-179.

Hagberg, S., "A Rapid Method for Determining Alpha-Amylase Activity," Cereal Chem, Mar. 1960, pp. 218-222.
Huang, N. et al., "Classification and Evolution of alpha-Amylase Genes in Plants," Proceedings of the National Academy of Sciences of the United States of America, Aug. 15, 1992, pp. 7526-7530, vol. 89, No. 16.
Johnson, C., "Rain Tolerant Wheat Varieties on the Way," Australian Grain, Dec. 1999-Jan. 2000, p. i.
Lecommandeur, D. et al., "Monoclonal Antibodies to Barley α-Amylase I: Production, Characterization, and Application to a Specific Immunoassay," Hybridoma, 1990, pp. 177-187, vol. 9, No. 2.
McLeary, B.V. et al., "Measurement of Cereal α-Amylase: A New Assay Procedure," Journal of Cereal Science, 1987, pp. 237-251, vol. 6.
"Measurement of α-Amylase Activity with the Amylograph," Enzymes, AACC Method 22-10, May 5, 1960, pp. 1-3.
"Measurement of α-Amylase Activity with the Rapid Visco Analyser," Enzymes, AACC Method 22-08, Nov. 8, 1995, pp. 1-4.
"Measurement of α-Amylase in Cereal Grains and Flours—Amylazyme Method," Enzymes, AACC Method 22-05, Nov. 3, 1999, pp. 1-5.
"Measurement of α-Amylase in Plant and Microbial Materials Using the Ceralpha Method," Enzymes, AACC Method 22-02, Oct. 17, 2001, pp. 1-5.
Meredith, P. et al., "Sprouted Grain," Chapter 5: Advances in Cereal Science and Technology, pp. 239-320, vol. VII.
NCBI Accession No. CAA33298.1 [Retrieved on Oct. 25, 2005]>.
NCBI Accession No. CAA33299.1 [Retrieved on Oct. 25, 2005].
Perten, J. et al., "Falling Number Experience Reviewed," pp. 569-576.
Rahmatullah, R.J. et al., "Nucleotide and Predicted Amino Acid Sequences of Two Different Genes for High-pI α-Amylases From Barley," Plant Molecular Biology, 1989, pp. 119-121, vol. 12.
Ringlund, K., "Differences in Falling Number at Constant Alpha-Amylase Activity," Third Int. Symp. Pre-harvest Sprouting Cereals, 1983, pp. 111-118.
Rogers, J.C., "Two Barley α-Amylase Gene Families are Regulated Differently in Aleurone Cells," The Journal of Biological Chemistry, Mar. 25, 1985, pp. 3731-3738, vol. 260, No. 6.
Sander, I. et al., "Development of a Two-Site Enzyme-Linked Immunosorbent Assay for α-Amylase from *Aspergillus oryzae* Based on Monoclonal Antibodies," Journal of Immunological Methods, 1997, pp. 93-101, vol. 210.
Skerritt, J.H. et al., "A Five-Minute Field Test for On-Farm Detection of Pre-Harvest Sprouting in Wheat," Crop Sci., May-Jun. 2000, pp. 742-756, vol. 40.
Skerritt, J. et al., "Trials Show Pre-Harvest Quality Test Works Well in the Field," Australian Grain, Jun.-Jul. 1999, pp. 38, 40.
Verity, J.C.K. et al., "Development of a Field Enzyme-Linked Immunosorbent Assay (ELISA) for Detecion of a α-Amylase in Preharvest-Sprouted Wheat," Cereal Chemistry, 1999, pp. 673-681, vol. 76, No. 5.

* cited by examiner

*Primary Examiner*—Bao-Thuy L Nguyen
(74) *Attorney, Agent, or Firm*—Baker Donelson Bearman, Caldwell & Berkowitz, PC

(57) ABSTRACT

Monoclonal antibody that specifically binds to alpha-amylase and is useful for detecting weather damage (i.e. preharvest sprouting) in cereal grain.

16 Claims, 10 Drawing Sheets

FIGURE 3

```
amy 1/13    MASKHLSLFLVLLGLSASLASGQVLFQGFNWESWKHNGGWYNFLMGKVDDIAAAGVTHVWLPPASQSVSEQGYMPGRLYDLDASKYGNKAQLKSLIGALH
185612      ----------
ADL
ALI
10413
15689                                                                                   ----------
15724                                                                                   ----------
15764                                                                                   ---------- amy 1/13    GKGVKALADIVINHRTAERKDGRGIYCIFEGGTPDARLDWGPHMICRDDRPYADGTGNPDTGADFGAAPDIDHLNPRVQKELVELLNWLRTDIGFDGWRF
185612                                                ----
ADL
ALI                                                                                 ----------
10413
15689                   ----------                                                                ----------
15724                   ----------                                                                ----------
15764                   ----------                                                                ---------- amy 1/13    DFAKGYSADVAKIYVDRSEASFAVAEIWTSLAYGDGKPNLNQDPHRQELVNWVNKVGGSGPGTTFDFTIKGILNVAVEGELWRLRGTDGKAPGMIGWWP
185612                                                                        ----------
ADL                                                                             ----------
ALI                                                                             ----------
10413                                                                           ----------
15689                                         ----------                        ----------
15724                                         ----------
15764                                         ---------- amy 1/13    AKAVTFVDNHDTGSTQHMWPFPSDRVMQGYAYILTHPGPPCIFYDHFFDWGLKEEIDRLVSIRTRQGIHSESKLQIIEADADLYLAEIDGKVTVKLGPRY
185612
ADL                                                              ----------
ALI
10413
15689                                                                                     ----------
15724                                                                                     ----------
15764 amy 1/13    DVGHLIPGGLKVAAHGKDYAIWEKI (SEQ ID NO: 4)
185612      ----------
ADL
ALI         ----------
10413
15689
15724
15764
```

MONOCLONAL ANTIBODIES TO ALPHA-AMYLASE

CROSS REFERENCE TO RELATED APPLICATIONS

This application is a divisional of U.S. application Ser. No. 09/830,876, filed Jul. 20, 2001 (International filing date Nov. 11, 1999), now U.S. Pat. No. 7,074,579 which is a 371 National Stage of International Application No. PCT/AU99/00995, filed Nov. 11, 1999, which claims the right of priority based on Australian application serial no. PP7058, filed Nov. 11, 1998, all of which are herein incorporated in their entirety by reference.

FIELD OF THE INVENTION

This invention relates to a two-site immunoassay for the qualitative or quantitative detection of alpha-amylase. The invention allows for the identification of "weather damage" in cereals (especially wheat).

BACKGROUND OF THE INVENTION

Weather damage or preharvest sprouting in wheat, is caused by the action of hydrolytic enzymes (amylases, proteases and lipases) in the grain endosperm. These enzymes (triggered by rain at or just before harvest), accelerate the breakdown of starch granules and protein in the endosperm of germinating grain (Meredith, P.; Pomeranz, Y. Advances in Cereal Science and Technology 7 (1985) 239-299). Wheat that is weather-damaged has a significantly lower market value as a result of being rendered unsuitable for human consumption. This is because the products that are made from sprouted wheat, for example breads, have grey colour, crumb texture, loaf structure and volume or in the case of noodles, poor colour and cooking qualities, due to the action of these hydrolytic enzymes, which include alpha-amylases (Orth, R. A.; Moss, H. J. Proceedings of the Fourth International Conference on Pre-harvest Sprouting, D. Mares (Ed.) Westview Press, Boulder, Colo., USA (1987) 167-175; Derera, N. F. (Ed.) Preharvest sprouting in cereals, CRC Press Inc., Boca Raton, Fla., USA (1989)).

At grain delivery to the silo or elevator or during harvesting, mixing of a small quantity of damaged grain with larger amounts of sound grain can lead to downgrading of all of the grain. The necessity for accurately discriminating sprouted from sound wheat highlights the need for a quick, easy and reliable test for preharvest sprouting. The most common method for detecting preharvest sprouting at elevators involves the measurement of alpha-amylase activity using the "Falling Number" method, in which the consequences of enzymic hydrolysis of starch caused by amylase production is assessed as the time required for a plunger to fall through a heated slurry of wholemeal and water (Hagberg, S. Cereal Chemistry 37 (1960) 218; Perten, H. Cereal Chemistry 41 (1964) 127-140). However, the capital cost of the instrument means that it is only feasible to install them at a limited number of mills or major grain silos or elevators. The method is also relatively low in throughput and results can be affected by variation in starch pasting characteristics (D'Appolonia, B. L.; Macarthur, L. A., Pisesookbuntererng, W.; Ciacco, C. F. Cereal Chemistry 59 (1982) 254-257; Ringlund, K. Proceedings of the Third International Symposium on Pre-Harvest Sprouting in Cereals, J. E. Kruger and D. E. LaBerge (Eds.) Westview Press, Boulder, Colo., USA, (1983) 111-118).

The cheaper option of visual assessment is both unreliable and not objective (Jensen, S. A.; Munck, L.; Kruger, J. E. Journal of Cereal Science 2(1984) 187-201), while other methods such as the Rapid ViscoAnalyzer (Ross, A. S.; Orth, R. A.; Wrigley, C. W. Proceedings of the Fourth International Symposium on Pre-Harvest Sprouting in Cereals, D. J. Mares (Ed.) Westview Press, Boulder, Colo., USA (1987) 577-583) and Near Infrared analysis (Czuchajowska, Z.; Pomeranz, Y. Preharvest Sprouting in Cereals 1992, M. K. Walker-Simmons and J. L. Ried (Eds.) American Association of Cereal Chemists, St Paul, Minn., USA (1992) 409-416), although faster, involve high capital cost. Near Infrared predictions of Falling Number are also of relatively low precision and can only discriminate relatively large differences in Falling Number (Osborne, B. G. Journal of the Science of Food and Agriculture, 35 (1984) 106-110; Czuchajowska, Z.; Pomeranz, Y.; Preharvest Sprouting in Cereals 1992, M. K. Walker-Simmons and J. L. Ried (Eds.) American Association of Cereal Chemists, St Paul, Minn., USA (1992) 409-416; Shashikumar, K.; Hazleton, J. L.; Ryu, G. H.; Walker, C. E. Cereal Foods World 38 (1993) 264-269). Direct enzyme activity assays for alpha-amylase (Barnes, W. C.; Blakeney, A. B. Die Starke 6 (1974) 193-197; McCleary, B. V.; Sheehan, H. Journal of Cereal Science 6 (1987) 237-251) are not suited for silo (elevator) or on-farm use due to a need for technical expertise and equipment such as waterbaths and filtration devices.

Immunoassays provide alternative methods for detection of preharvest sprouting through the use of antibodies that are specific for alpha-amylase isozymes. Alpha-amylases are considered to be the most appropriate targets for a test because: 1. they are relatively abundant, 2. they are synthesized early in the preharvest sprouting sequence (Corder, A. M., and Henry, R. J. Cereal Chemistry 66 (1989) 435-439), 3. they are responsible for many of the quality defects that occur when end products are prepared from sprouted wheat, and 4. the basis of the measurements in the "industry standard test" (Falling Number) is changes in the viscosity of a wholemeal-water slurry due to the presence of carbohydrate-degrading enzymes such as amylases. Earlier research has shown that specific antisera can be developed for separate recognition of the two major groups of alpha-amylase isozymes (Daussant, J.; Renard; H. A. Cereal Research Communications 4 (1976) 201-212; Lazarus, C. M.; Baulcombe, D. C.; Martienssen, R. A. Plant Molecular Biology 5 (1985) 13-24). Immunoassay techniques have an added potential advantage over enzyme activity assays, in that by using appropriate amylase antibodies it should be possible to specifically measure different amylase isozyme families. Immunoassay kits are generally quite robust and suitable for shipping and use in harsh environments, and can be used by individuals with little training. Such tests could not only be used by grain handlers or traders at silo (elevator) delivery of grain, but also by individual wheatgrowers. This would allow them to detect sprouting on-farm prior to harvesting in order to prevent contamination of sound wheat by sprouted grain.

The most sensitive, specific and quantitative immunoassays require the use of both a solid-phase bound antibody and a labelled detection antibody in a "two-site" assay. The detection antibody may be labelled with an enzyme, coloured particle or sol, or radioactive element or fluorophore. However, for field use without special equipment, the most useful methods are those in which the test result can be interpreted visually. The present invention relates to the development of two-site immunoassays for the qualitative or quantitative detection of alpha-amylase.

DISCLOSURE OF THE INVENTION

Thus, in a first aspect, the present invention provides a two-site immunoassay for the qualitative or quantitative detection of alpha-amylase in a test sample, said immunoassay comprising;

(i) exposing said test sample to a first ("capture") antibody or fragment thereof which specifically or preferentially binds to a first epitope on said alpha-amylase, under conditions permitting binding of said first antibody or fragment thereof to alpha-amylase if present, (ii) subsequently exposing bound alpha-amylase, if any, to a second ("detection") antibody or fragment thereof which specifically or preferentially binds to a second epitope on said alpha-amylase that is distinct from said first epitope, under conditions permitting binding of said second antibody or fragment thereof to said bound alpha-amylase, and (iii) detecting any binding of said second antibody or fragment thereof to said bound alpha-amylase, wherein either of said first or second epitopes is an epitope comprising one or more of the amino acid sequences; IDRLVSIRTRGQIHS (SEQ ID NO: 1), CRDDRPYADG (SEQ ID NO: 2), VNWVNKVGGS (SEQ ID NO: 3) and variants thereof showing ≧80%, more preferably ≧90%, sequence identity.

Preferred variant sequences include those that differ from the amino acid sequences IDRLVSIRTRGQIHS (SEQ ID NO: 1), CRDDRPYADG (SEQ ID NO: 2) and VNWVNKVGGS (SEQ ID NO: 3) in one or more conservative amino acid substitution(s). The conservative amino acid substitutions envisaged are:— G,A,V,I,L,M; D,E; N,Q; S,T; K,R,H; F,Y,W,H; and P,Nα-alkalamino acids.

Preferably, either of said first or second epitopes is a conformational epitope comprising one or more of the amino acid sequences; IDRLVSIRTRGQIHS (SEQ ID NO: 1), CRDDRPYADG (SEQ ID NO: 2) and VNWVNKVGGS (SEQ ID NO: 3).

More preferably, either of said first or second epitopes is a conformational epitope comprising all of the amino acid sequences; IDRLVSIRTRGQIHS (SEQ ID NO: 1), CRDDRPYADG (SEQ ID NO: 2) and VNWVNKVGGS (SEQ ID NO: 3).

The two-site immunoassay of the present invention may be performed in accordance with any of the formats well known in the art. Particularly preferred formats include the sandwich enzyme-linked immunosorbent assay (ELISA) and immunochromatography (IC).

In the ELISA format, the first antibody or fragment thereof is provided bound to a solid support such as a microwell plate, membrane, beads, particles or suitable sensor. It is preferable to use a blocking agent to prevent non-specific binding and to conduct the ELISA assay with washing steps as is well known in the art.

In the IC format, the second antibody or fragment thereof is provided bound to a solid support such as porous test strip. As is well known in the art, it is possible to conduct IC assays without the use of a blocking agent or washing steps.

At least one of the first and second antibodies or fragments thereof is/are preferably selected from monoclonal antibodies or fragments thereof (e.g. Fab and F(ab')$_2$), recombinant antibodies or fragments thereof and recombinant antibody fragments (e.g. scFv). These provide significant commercial advantages over, for example, polyclonal antibodies. First, they recognise a limited number of epitopes and, for that reason, do not form aggregating complexes which can compromise ELISA or IC performance. Secondly, they are constant and reproducible reagents.

Detection of binding of the second antibody or fragment thereof may be achieved through the use of a readily detectable label such as a detectable enzyme (e.g. horseradish peroxidase or alkaline phosphatase), radioisotope (e.g. $P^{32}$ or $S^{35}$) or luminescent or fluorescent label. Detection of binding of the second antibody might also be achieved through other means such as immunochromatography and agglutination.

The two-site immunoassay of the present invention is particularly suitable for the qualitative or quantitative detection of alpha-amylase in a cereal grain (e.g. wheat including bread wheat (*Triticum aestivum*), durum wheat (*Triticum turgidum* var. durum) and club wheat (*Triticum compactus*); rye (*Secale cereale*); triticale (*Triticosecale* species); barley (*Hordeum vulgare*) and related cereals (i.e. members of the Triticeae family), and thereby provides for the qualitative or quantitative detection of weather damage.

The test sample utilised in a two-site immunoassay for this purpose is preferably an aqueous extract from grain or, more preferably, grain meal or flour. As is described in greater detail below, alpha-amylase may be readily extracted from grain meal or flour with a dilute solution of NaCl or CaCl$_2$.

When used for the quantitative detection of alpha-amylase in cereal grain, the two-site immunoassay further comprises a step of comparing the level of detected binding of the second antibody or fragment thereof against a suitable standard. Preferably, the level of detected binding of the second antibody or fragment thereof is positively correlated with alpha-amylase enzyme activity and negatively correlated with Falling Number.

In a second aspect, the present invention provides a monoclonal antibody or fragment thereof, recombinant antibody or fragment thereof, recombinant antibody fragment or binding partner which specifically or preferentially binds to an epitope on alpha-amylase comprising one or more of the amino acid sequences; IDRLVSIRTRGQIHS (SEQ ID NO: 1), CRDDRPYADG (SEQ ID NO: 2), VNWVNKVGGS (SEQ ID NO: 3) and variants thereof showing ≧80%, more preferably ≧90%, sequence identity.

Preferred variant sequences include those that differ from the amino acid sequences IDRLVSIRTRGQIHS (SEQ ID NO: 1), CRDDRPYADG (SEQ ID NO: 2) and VNWVNKVGGS (SEQ ID NO: 3) in one or more conservative amino acid substitution(s). The conservative amino acid substitutions envisaged are:— G,A,V,I,L,M; D,E; N,Q; S,T; K,R,H; F,Y,W,H; and P,Nα-alkalamino acids.

Preferably, the monoclonal antibody or fragment thereof, recombinant antibody or fragment thereof, recombinant antibody fragment or binding partner of the present invention specifically or preferentially binds to a conformational epitope comprising one or more of the amino acid sequences; IDRLVSIRTRGQIHS (SEQ ID NO: 1), CRDDRPYADG (SEQ ID NO: 2) and VNWVNKVGGS (SEQ ID NO: 3).

More preferably, the monoclonal antibody or fragment thereof, recombinant antibody or fragment thereof, recombinant antibody fragment or binding partner of the present invention specifically or preferentially binds to a conformational epitope comprising all of the amino acid sequences; IDRLVSIRTRGQIHS (SEQ ID NO: 1), CRDDRPYADG (SEQ ID NO: 2) and VNWVNKVGGS (SEQ ID NO: 3).

In a third aspect, the present invention provides a kit for performing a two-site immunoassay for the qualitative or quantitative detection of alpha-amylase in a test sample, said kit comprising a container or solid support including a monoclonal antibody or fragment thereof, recombinant antibody or fragment thereof, recombinant antibody fragment or binding partner according to the second aspect.

For performing a two-site immunoassay for the qualitative or quantitative detection of alpha-amylase in a cereal grain, the kit may further comprise a container including an aqueous extraction agent for extracting alpha-amylase from grain, grain meal or flour.

Throughout this specification, unless the context requires otherwise, the term "comprise", or variations such as "comprises" or "comprising", will be understood to imply the inclusion of a stated element, integer or step, or group of elements, integers or steps, but not the exclusion of any other element, integer or step, or group of elements, integers or steps.

The term "specifically binds" as used herein is intended to refer to binding characteristics of antibodies and fragments thereof which bind exclusively to the defined epitope on alpha-amylase or with only negligible cross-reaction with epitopes on other cereal grain substituents.

The term "preferentially binds" as used herein is intended to refer to binding characteristics of antibodies and fragments thereof which bind strongly to the defined epitope on alpha-amylase and to a lesser extent with epitopes on other cereal grain substituents.

The term "recombinant antibody", refers to an antibody that has been expressed from a host cell culture that has been transformed with an isolated, manipulated or synthesised expressible gene encoding the antibody. Methods for producing such recombinant antibodies are described in Pluckthun, A. Bio/Technology 9, 545-551 (1991).

The term "recombinant antibody fragment", refers to an antibody fragment that has been expressed from a host cell culture that has been transformed with an isolated or synthesised expressible gene encoding the antibody fragment. Examples of such recombinant antibody fragments are single chain Fv (scFv) antibody fragments. Methods for producing scFvs are described in Pluckthun, A. Bio/Technology 9, 545-551 (1991) and U.S. Pat. No. 4,946,778.

The invention is hereinafter described by reference to the accompanying figures and the following non-limiting examples describing the preparation and characterisation of suitable antibodies, their utilisation in immunoassays, and the use of immunoassays to quantify differences in alpha-amylase in wheat samples.

BRIEF DESCRIPTION OF THE ACCOMPANYING FIGURES

FIG. 1 shows the titration of monoclonal and polyclonal antibodies to alpha-amylase using indirect ELISA. ELISA plates were coated with 1 µg purified amylase per microwell (high plus low pI isozymes from cv. Janz). Data are the mean±SD of 3 replicates.

FIG. 3 shows amino acid sequences with high-pI alpha-amylase clone Amy-1 13/1 recognised by seven antibodies.

Figure 5A:
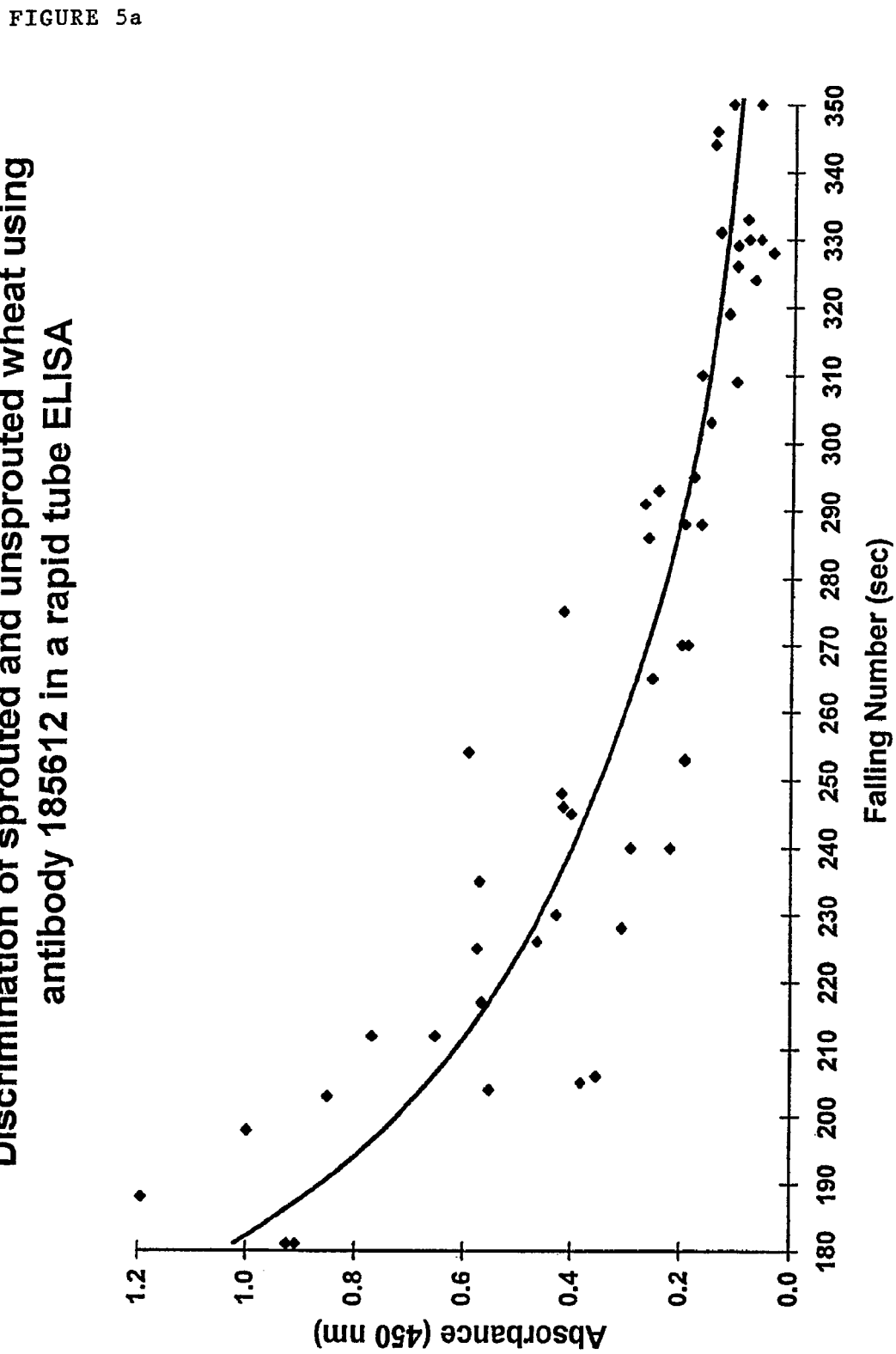
Figure 5B:
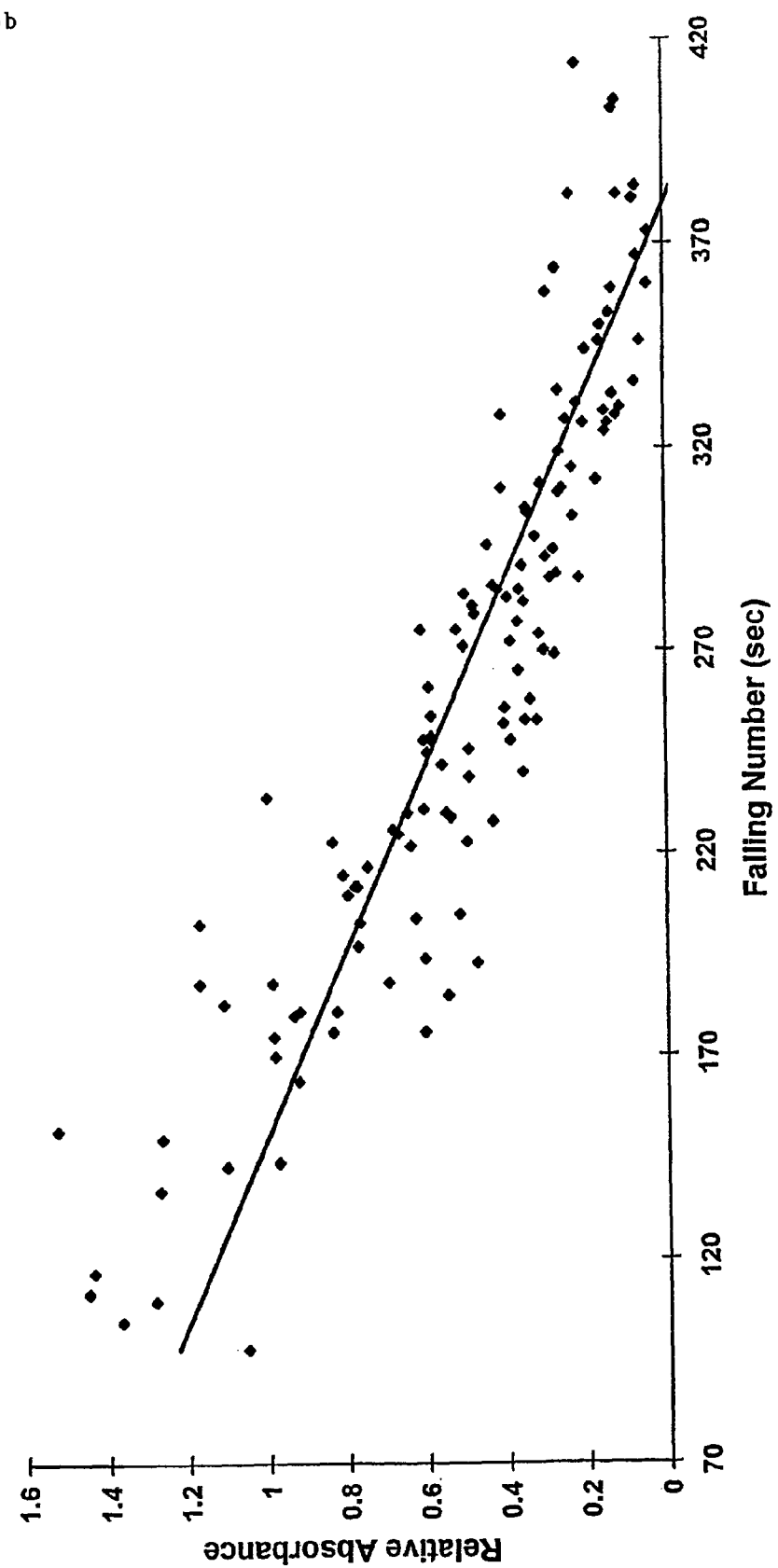

FIG. 5 shows the discrimination of sprouted and unsprouted wheat through relationships between ELISA absorbance using a rapid tube and Falling Number for wheat samples from elevators in Queensland, with A. 59 grain samples and an assay using immobilised ALI antibody and enzyme-labelled 185612, and B. 130 grain samples and an assay using immobilised ALI antibody and enzyme-labelled ALI antibody. Samples were analyzed in duplicate in two separate runs and raw absorbances standardized to the absorbance of a standard of Falling Number 187 units included in each run.

Figure 6:
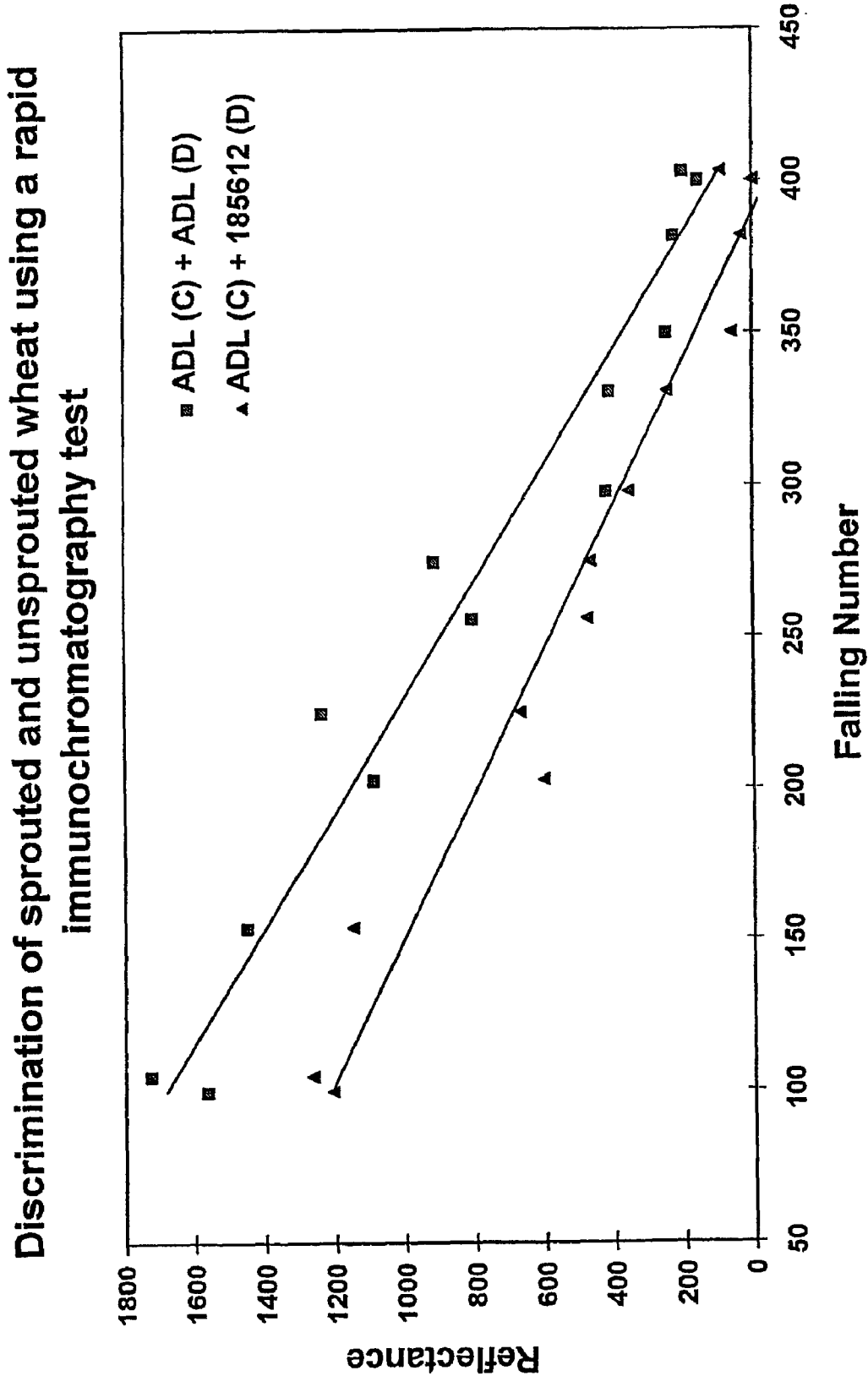

FIG. 6 shows the relationship between immunochromatography band intensity (reflectance) and Falling Number for 13 wheat samples using antibody ADL as the capture (C) antibody plus 185612 or ADL as gold-labelled detection (D) antibody.

Figure 7:
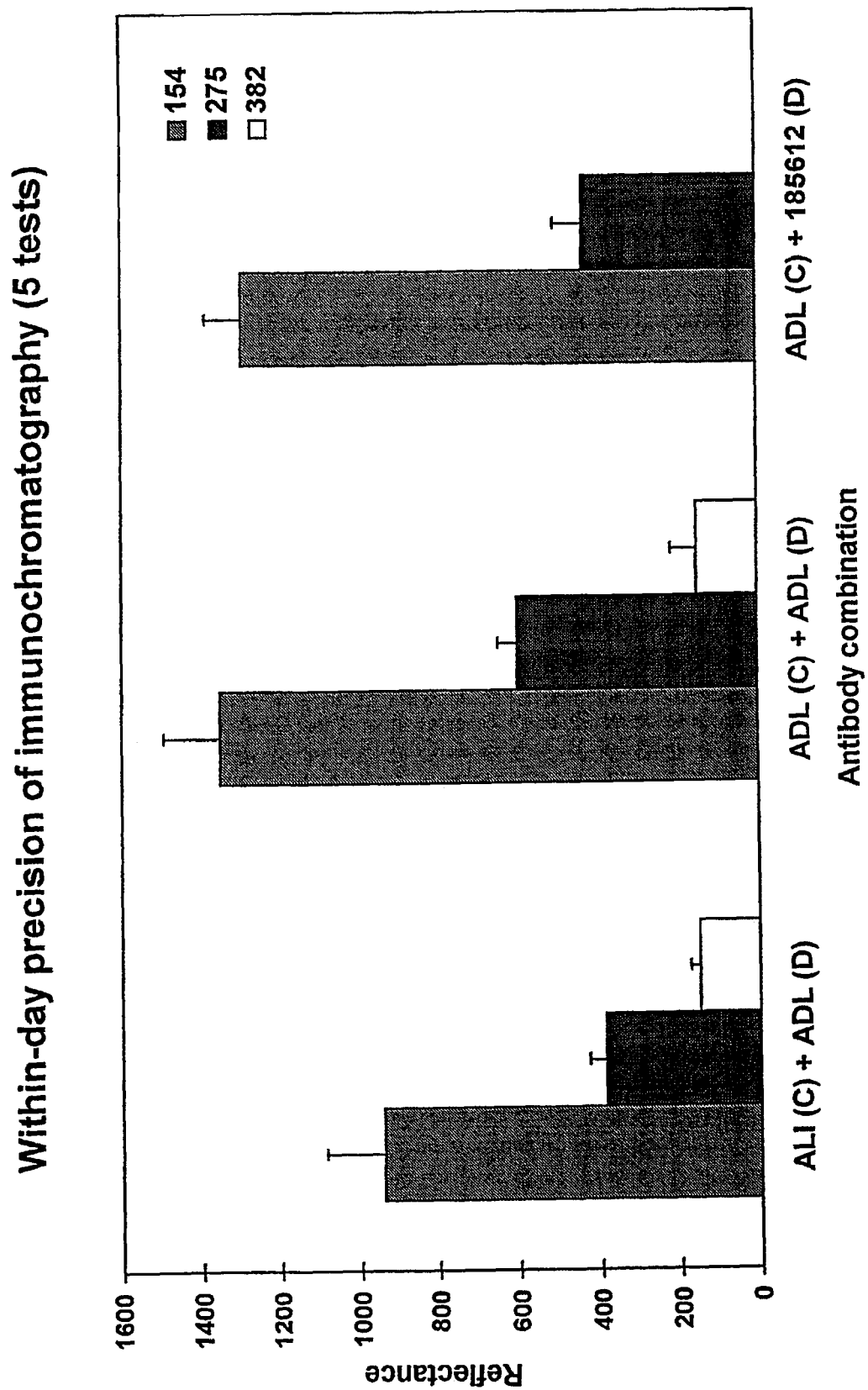

FIG. 7 shows the within-day precision of immunochromatography tests (mean±standard deviations of results of 5 tests) using different antibody combinations and moderately sprouted (Falling Number 154 seconds), mildly sprouted (Falling Number 275 seconds) and unsprouted (Falling Number 382 seconds) wheat grain.

EXAMPLES

Example 1

Production of Antibodies to Alpha-Amylases and Analysis of their Specificities

Amylase Purification

Grain from two wheat cultivars (Janz and Osprey) was germinated for 4 days at 20° C. Germinated grain was frozen by immersion in liquid nitrogen and freeze-dried. Roots and shoots were removed and the grain was ground into wholemeal flour using a Jupiter Electric Cereal Grinder (JUPITER, Schorndorf, Germany). Alpha-amylase was extracted by stirring wholemeal flour in 20 mM sodium acetate buffer, pH 5.5 containing 1 mM $CaCl_2$ (extraction buffer) at 5° C. for 1 hour. All subsequent steps were performed at 5° C. The extract was centrifuged (48,000 g, 30 min), and the resulting supernatant subjected to a 20-60% ammonium sulfate precipitation. The material that precipitated between these salt concentrations was redissolved and dialyzed against the extraction buffer. The dialyzed extract was filtered using a 0.8 µm filter and purified using affinity chromatography.

A mixture of both high and low pI isozymes of alpha-amylase was isolated by β-cyclodextrin affinity chromatography. The affinity column (12×3 cm) consisted of epoxy-activated Sepharose 6B coupled to cyclohepta-amylose (β-cyclodextrin); Sepharose 6B was activated using 1,4-butanedioldiglycidyl ether (Sigma, St Louis, Mo.) according to the methods of Sundberg, L.; Porath, J. Journal of Chromatography 90 (1974) 87-98) and coupled to cycloheptaamylose using the method of Vretblad, P. FEBS Letters 47 (1974) 86-89. Alpha-amylase was eluted with 20 mM sodium acetate buffer (pH 5.5), containing 1 mM $CaCl_2$, 0.5 M NaCl and 8 mg/mL of cycloheptaamylose, and dialysed against 10 mM sodium acetate buffer (pH 5.5), containing 1 mM $CaCl_2$ and reduced in volume by ultrafiltration.

Separation of high and low pI isozymes of alpha-amylase was achieved using one of three methods, either 1) ion-exchange chromatography (Lecommandeur, D. Journal of Chromatography 441 (1988) 436) using CM-Sepharose CL-6B, equilibrated with 20 mM acetate buffer, pH 4.8, containing 1 mM calcium chloride and eluted with a 0-0.3 M NaCl gradient, 2) preparative isoelectric focussing using a Rotofor device (Hochstrasser A. C. et al; Applied and Theoretical Electrophoresis, 1 (1991) 333-337) and pH 3-10 carrier ampholytes (Biorad, Hercules, Calif., USA), or 3) immunoaffinity chromatography using a column prepared by coupling a monoclonal antibody prepared to the high pI alpha-amylase isozyme of barley (Gibson, C. E., Evans, D. E., MacLeod, L. C., Symons, M. H., Marschke, R. J., Jarratt, S., Dalton, M. R., Lance, R. C. M., Skerritt, J. H., Henry, R. J. and Fincher, G. B. Proceedings of the 44th Australian Cereal Chemistry Conference, Royal Australian Chemical Institute, Melbourne, 44 (1994) 174-179), to CNBr-activated Sepharose 4B (Pharmacia, Uppsala, Sweden). A crude extract of amylase purified using the cycloheptaamylose method, was dialyzed against the immunoaffinity column equilibration buffer (50 mM Tris, pH 7.6 containing 5 mM $CaCl_2$ and 0.5 M NaCl). High pI alpha-amylase was eluted with 2.5 M KSCN containing 5 mM $CaCl_2$ and 0.5 M NaCl. The unbound fraction (thought to contain low pI amylase) was collected during loading onto the column. This fraction along with the eluted enzyme was dialyzed and concentrated as described above.

The purity of alpha-amylase prepared from crude wheat extract by affinity chromatography was shown by SDS-PAGE to contain a single band with an approximate molecular weight of 44,000, in agreement with previous reports (Hill, R. D.; MacGregor, A. W. Advances in Cereal Science and Technology 9 (1988) pp 217-261. Isoelectric focusing of purified alpha-amylase, revealed the presence of approximately 6 to 8 bands between pH 6-7 (high pI isozymes, products of alpha-amy 1 genes on group 6 chromosomes) and approximately four to six less strongly stained bands between pH 4.5-5.5 (low pI isozymes; products of alpha-amy 2 genes on group 7 chromosomes). Two hundred grams of germinated grain yielded approximately 24 mg of a mixture of high and low pI amylase and approximately 14 mg of high pI amylase.

Production of Monoclonal and Polyclonal Antibodies to Alpha-Amylase

Polyclonal antisera were produced to the high pI amylase isozymes and to a mixture of both the high and low pI isozymes of the enzyme. Rabbits were given an initial injection of 1 mg protein (mixed 1:1 in Freund's Complete Adjuvant, FCA; Sigma) split between three injection sites in the muscles of both hind legs and subcutaneously in the neck area. Rabbits were boosted 14 and 28 days after the initial injection (500 µg protein in Freund's Incomplete Adjuvant, FICA), and blood was collected 10 days after the third booster. Sera were tested for antibodies to alpha-amylase using indirect ELISA (see below), and rabbits were boosted thereafter at monthly intervals with 500 µg protein in FICA. Antibodies were purified from rabbit sera using Gamma Bind IgG affinity chromatography.

Monoclonal antibodies (MAb) to-alpha amylase were produced by immunizing BALB/c mice with a mixture of both high and low pI isozymes of the enzyme (purified separately from both Janz and Osprey cultivars). Mice were given an initial intraperitoneal (IP) injection of 200 µg total protein mixed 1:1 in FCA. This was followed by two IP injections (in FICA) of 100 µg protein at 2-week intervals. At 4 weeks after the third injection, mice were given a final IP booster of 200 µg amylase per mouse 3 days prior to fusion. The quantity of enzyme used for immunisation was optimised in initial experiments in which 3 groups of mice (2 mice/group) were immunised initially with either 200, 40 or 10 µg total protein, and subsequently with either 100, 20 or 5 µg total protein. Blood was collected from all mice by tail bleed at 10 days after the third injection and tested for antibodies against alpha-amylase by indirect ELISA. Hybridoma production was carried out according to the general methods of Skerritt, J. H.; and Underwood, P. A. Biochimica et Biophysica Acta 874 (1986) 245-254, and supernatants secreted by the resulting hybridoma cells were tested for specificity to alpha-amylase using indirect ELISA (see below). Positive cell lines were subcloned cloned and expanded by ascites, and antibodies isotyped using a Mouse-Typer Sub-isotyping Kit (Bio-Rad, Hercules, Calif.). Several high-titre independent cell lines which secreted high-titer antibodies were isolated: 15764, 15689, 10185 and 10413 (all IgM,κ) and 15724 and 185612 were $IgG_1$, κ.

Monoclonal and polyclonal antibodies were tested for specificity for alpha-amylase using semi-dry immunoblotting of SDS-PAGE gels and passive immunoblotting of isoelectric focussing (IEF) gels. SDS-PAGE gels (12% T, 2% C gel, run 1500 Vhr) were loaded with a crude extract of alpha amylase and electrophoresis and immunoblotting (for 4 h at 250 mA/gel) onto nitrocellulose was carried out according to Andrews, J. L.; and Skerritt, J. H. Journal of Cereal Science, 23 (1996) 61-72. IEF used 7.5% T, 3% C polyacrylamide gels (0.5 mm) with an ampholyte pH gradient of 3-10. 1 M sodium hydroxide and 1 M phosphoric acid were used as cathode and anode solutions respectively, and gels were run at 4° C. under constant power (8-10 W) for 3 hours after loading with purified α-amylase. Membranes from both procedures were blocked with 3% (w/v) bovine serum albumin (BSA) in 50 mM sodium phosphate-buffered saline, pH 7.2 (PBS), probed with MAbs or PAbs, and detected with alkaline phosphatase-labeled second antibodies from Promega (Madison, Wis., USA).

On immunoblots of SDS-PAGE gels, both the polyclonal antiserum to high/low pI amylase and to high pI amylase primarily detected the $M_r$ 44,000 polypeptides corresponding to alpha-amylase. Weak reaction with other polypeptides in the $M_r$ 21,500-66,000 range (possibly fragments of alpha-amylase) was also seen. IEF immunoblots showed that the polyclonal antisera recognised both the high and low pI isozymes; the reaction of the antiserum to high pI amylases was somewhat less intense with the low pI isozymes than the corresponding reaction of the high/low pI amylase antibody. Even though the wheat monoclonal antibodies were produced by immunizing mice with a mixture of both high and low pI isozymes of amylase, only one of the six antibodies (10581) detected both groups of isozymes; the remaining ones bound the high pI group only.

Example 2

Characterisation of Antibody Performance in ELISAs for Alpha-Amylase in Wheat

Indirect and Direct ELISAs

Figure 1:
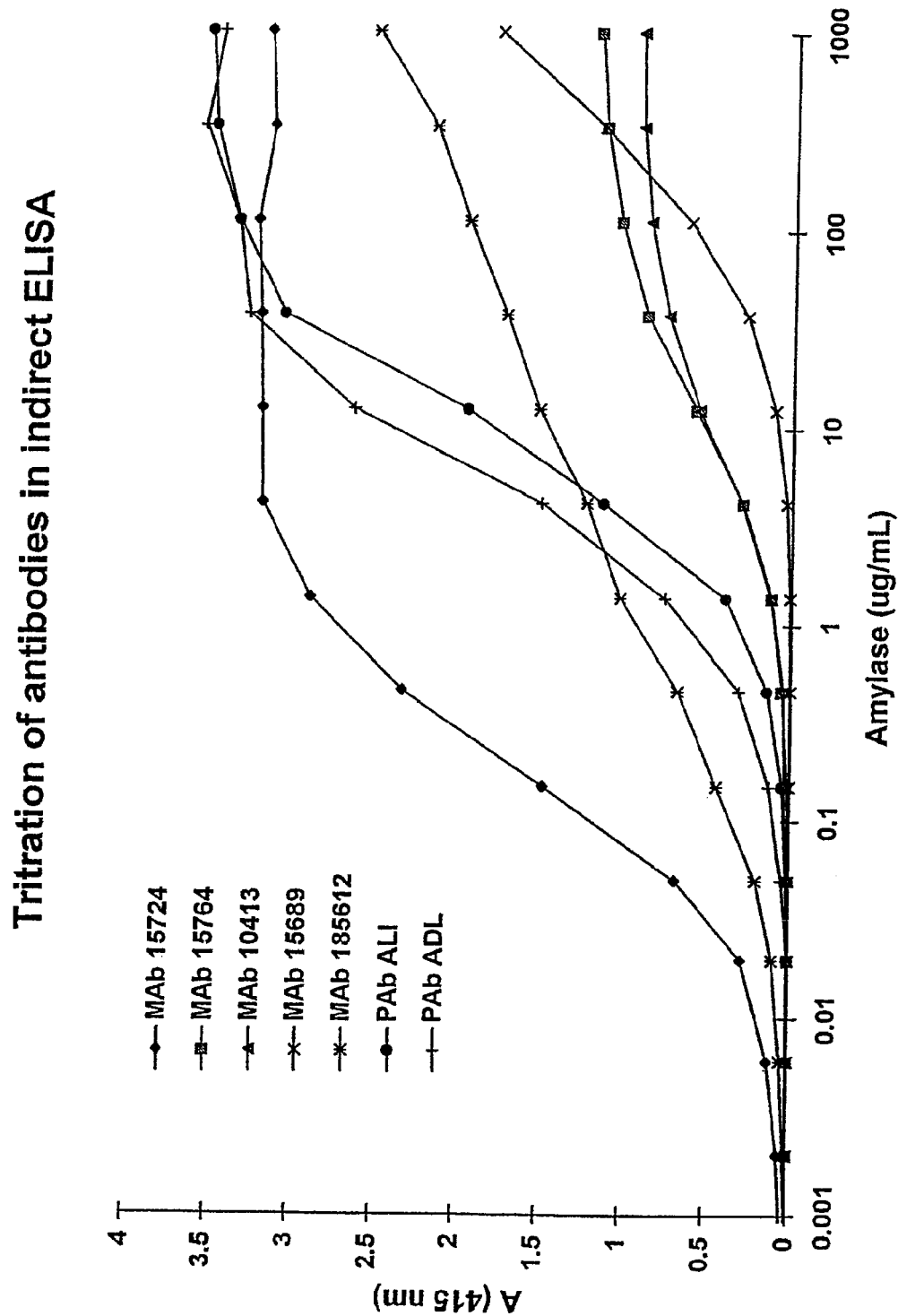

Antibodies were purified using either Gamma Bind (Pharmacia) Protein G affinity chromatography (IgG isotypes) or ammonium sulfate precipitation (IgM isotypes). For use in direct ELISA, epitope mapping and as detecting conjugates in two-site ELISA, antibodies were coupled to horseradish peroxidase (Boehringer-Mannheim, Germany) using a method modified from Nakane, P. K.; and Kawaoi, A. (Journal of Histochemistry and Cytochemistry 22 (1974) 1084-1091). Antibodies were initially titrated by indirect and direct ELISA, before being evaluated for their ability to capture and detect alpha-amylase in sandwich ELISA. In the indirect and direct assays, 96 well plates (Nunc Maxisorp, Roskilde, Denmark) were coated for 16 h at 20° C. with 100 µL of purified alpha-amylase antigen at 1 µg/well in 50 mM carbonate buffer, pH 9.6. Wells were then washed three times with PBS—0.05% Tween 20 (PBST), and non-specific binding sites were blocked with 1% BSA in PBS for 1 h at room temperature. Microwell-bound antigen was incubated for 90 min with 100 µL of antibody solution diluted in 1% BSA in PBS and then washed three times with PBST. This was followed by a 30 min incubation with either 100 µL/well peroxidase-labelled rabbit anti-mouse or goat anti-rabbit immuno-globulins (DAKO, Glostrup, Denmark) diluted 1:2000 and 1:400 respectively in 1% BSA in PBS. After four washes, 150 µL substrate-chromogen (2 mM 2,2'-azino-bis-3-ethylbenzthiazoline sulfonic acid (Sigma) in 0.1 M sodium citrate buffer, pH 4.5, containing 0.003% $H_2O_2$ (ABTS)), was added and plates incubated for 20 min at room temperature. The enzyme reaction was terminated by the addition of 50 µL oxalic acid (3%, w/v), and absorbance values were measured at 414 nm. Titration against purified alpha-amylase using indirect ELISA (FIG. 1) indicated that each of all the antibodies detected alpha-amylase with high sensitivity in this assay format.

Sandwich ELISAs

For sandwich ELISA, plates were coated for 16 h at 20° C. with 100 µL of either purified monoclonal antibodies or polyclonal antibodies at 1 µg/well in 50 mM carbonate buffer, pH 9.6. All subsequent steps were carried out at 20° C. The wells were washed 3 times with PBST and non-specific binding sites blocked with 1% BSA in PBS for 1 h. Purified alpha-amylase was serially diluted in 1% BSA in PBST, added to the wells (100 µl/well), and incubated for 1 h. After washing 3 times with PBST, 100 µL of HRP-labeled monoclonal antibody or polyclonal antibody diluted in 1% BSA in PBST was added to all wells and incubated for 30 min. The dilution of labeled antibody used had been previously determined by direct ELISA to provide an absorbance of between 1.0 and 1.5. Plates were washed as before and ABTS substrate was added to all wells. The reaction was stopped after 20 min and absorbance values were measured at 415 nm. Samples were analyzed in triplicate and the absorbance of blank wells (no addition of alpha-amylase) was subtracted from the absorbance of each well.

Figure 2:
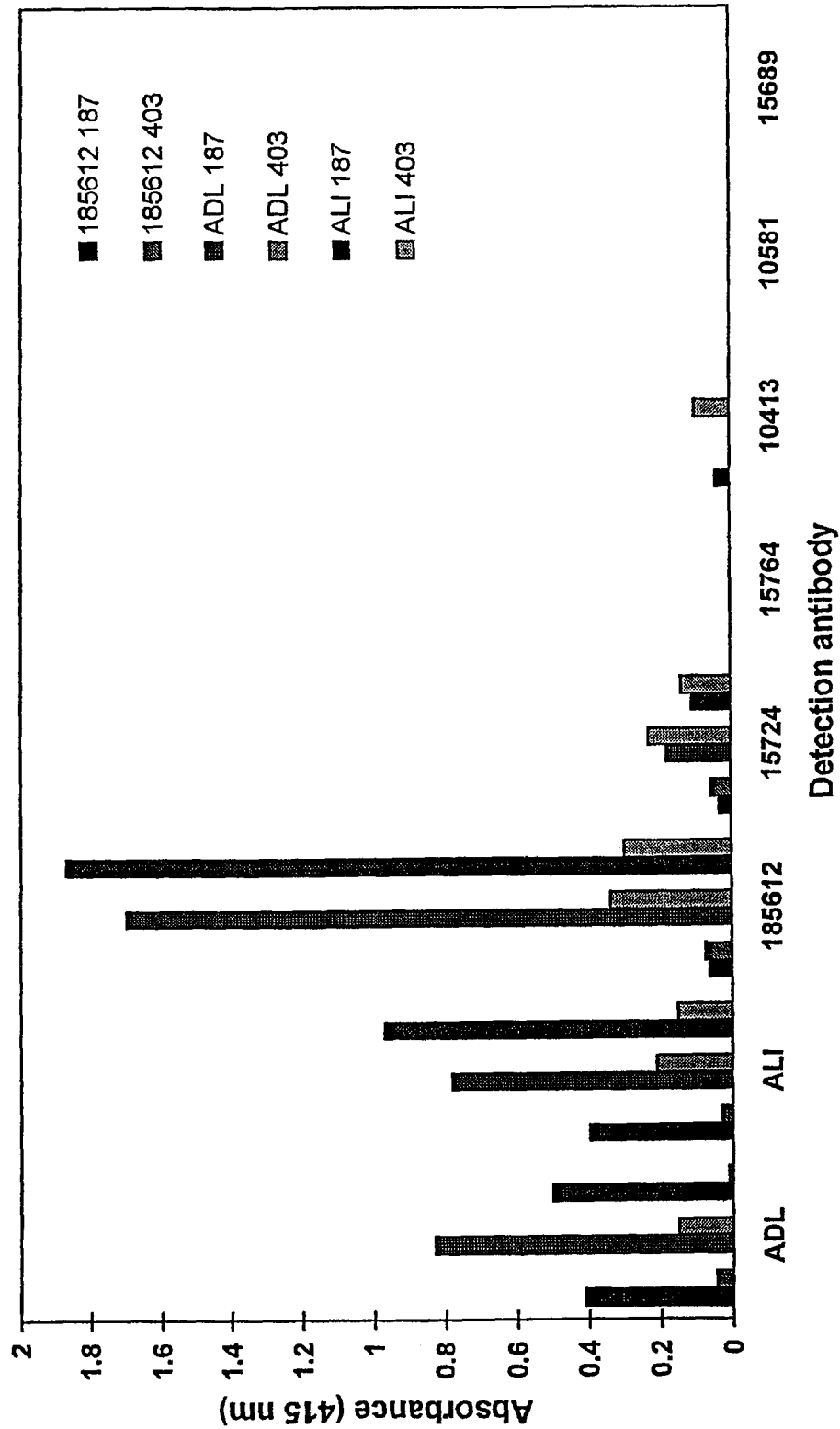
FIG. 2 shows the performance of antibody combinations in microwell two-site ELISAs with extracts of an unsprouted (Falling Number 403) and moderately sprouted (Falling Number 187) sample. Data are shown for three capture antibodies (185612, ADL, ALI) and eight detection antibodies.

All possible combinations of monoclonal and polyclonal antibodies were tested initially as capture and/or detection antibodies in the plate sandwich ELISA, using a wide range of concentrations (0.001-10 ug/mL) of purified amylase. Each polyclonal antibody functioned well as either a capture or detection antibody when used in conjunction with either the same antibody or another polyclonal antibody. Alpha-amylase was sensitively detected with a limit of detection (absorbance of 0.1 above background) of about 1 ng/mL, for either high pI amylase or high/low pI amylase. One monoclonal antibody (185612) also functioned as either a capture or detection antibody when used in conjunction with a polyclonal antibody (FIG. 2). However, the other monoclonal antibodies did not function as either capture or detection reagents; i.e. there was no difference between the absorbance of wells to which amylase had been added and the blank wells which contained no enzyme. Similarly negative results were obtained when these monoclonal antibodies were immobilised through rabbit immunoglobulins to mouse immunoglobulins rather than by direct adsorption to the solid phase. Thus, although the monoclonal antibodies were specific for alpha-amylase on immunoblots and sensitively detected the enzyme in indirect ELISAS, they failed to detect amylase in a plate sandwich ELISA. Use of higher antibody coating levels (up to 10 µg/well) and different coating buffers (e.g. phosphate-buffered saline, pH 7.2) did not effect antibody performance. A similar pattern of antibody performance was also noted in the rapid tube ELISA (Example 3) and immunochromatography formats (Example 4).

Characterisation of the Epitopes Recognised by Anti-Amylase Antibodies

The ability of only one of the monoclonal antibodies (185612) to detect alpha-amylases in the sandwich ELISA format as either capture or detection antibody raised the possibility that it may recognise an epitope in the amylase sequence that has a distinctive sequence and other properties from the epitopes in the other monoclonal antibodies. Firstly, to identify the linear epitopes recognised by the antibodies, a series of decapeptides with pentamer overlaps was synthesised corresponding to the entire coding region of the high pI alpha-amylase from wheat (clone amy 1/13 of Baulcombe, D. C.; Huttly, A.; Martienssen, R. A.; Barker, R. A.; Jarvis, M. G. Molecular and General Genetics 209 (1987) 33-40). This is a representative of the isozyme family which is preferentially expressed in wheat grain during germination (Lazarus, C. M.; Baulcombe, D. C.; Martienssen, R. A. Plant Molecular Biology 5 (1985) 13-24; Cejudo, F. J.; Cubo, M. T.; Baulcombe, D. C. Plant Science 106 (1995) 207-213). The decapeptides were prepared by solid-phase peptide synthesis on the tips of primed pins in an 8×12 array for direct testing in microwell plates, and the binding of five monoclonal and two polyclonal antibodies analysed using indirect ELISA. Non-specific antibody binding to the pins was blocked by incubation for 1 hour at 20° C. in 2% BSA in 0.15 M NaCl-10 mM sodium phosphate, pH 7.2 containing 0.05% Tween 20. The pins were transferred to wells containing peroxidase-labelled antibodies (diluted to provide a maximal absorbance of about 1.0) in 2% BSA in 0.15 M NaCl-10 mM sodium phosphate, pH 7.2 containing 0.05% Tween 20 and incubated for 1 hour at 20° C. with shaking, before being washed four times in 0.15 M NaCl-10 mM sodium phosphate, pH 7.2. Antibody binding to specific peptides was revealed by incubation in 2 mM diammonium 2,2'-azino-bis(3-ethylbenzthiazoline-6-sulfonic acid—0.003% (w/v) hydrogen peroxide in 50 mM sodium citrate, pH 4.5 for 40 minutes at 20° C. Replicate assays were performed to ensure that consistent results were obtained.

The antibodies strongly bound only a small number of peptide sequences in the high pI alpha-amylase sequence (FIG. 3). Antibody 185612, which functions as either capture or detection antibody in two-site assays, detected three main sequence regions. It most strongly recognised two arginine-rich sequences, which also contain other charged amino acids, especially aspartate in the case of the second amino sequence: IDRLVSIRTRGQIHS and CRDDRPYADG. In addition, a valine-rich peptide was detected: VNWVNKVGGS. A polyclonal antiserum to high pI alpha-amylase (ALI) also detected the IDRLVSIRTRGQIHS and VNWVNKVGGS sequences, as well as several other epitopes, in keeping with the polyclonal nature of the antiserum. A second polyclonal antiserum (ADL), prepared to a mixture of high and low pI alpha-amylases, also detected the VNWVNKVGGS sequence, along with several others (FIG. 3). Four monoclonal antibodies which sensitively detected alpha-amylase in indirect or direct ELISA but not two-site assays, detected epitopes that were distinct from those recognised by antibody 185612 (FIG. 3). In some cases the polyclonal antisera also recognised some of the same epitopes, suggesting that there are immunodominant regions in the alpha-amylase sequence. One antibody, 10413, recognised a peptide (KVGGSGPGTT) (SEQ ID NO: 5) that had a partial overlap with the valine-rich peptide recognised by antibody 185612 and the polyclonal antisera (VNWVNKVGGS). However, since 10413 did not bind to VNWVNKVGGS its epitope is clearly also distinct. Thus, these results indicate that the antibodies which function in the two-site assay recognise distinct epitopes from those recognised by other antibodies specific for alpha-amylase, but which do not function in the two-site assay.

Figure 4A:
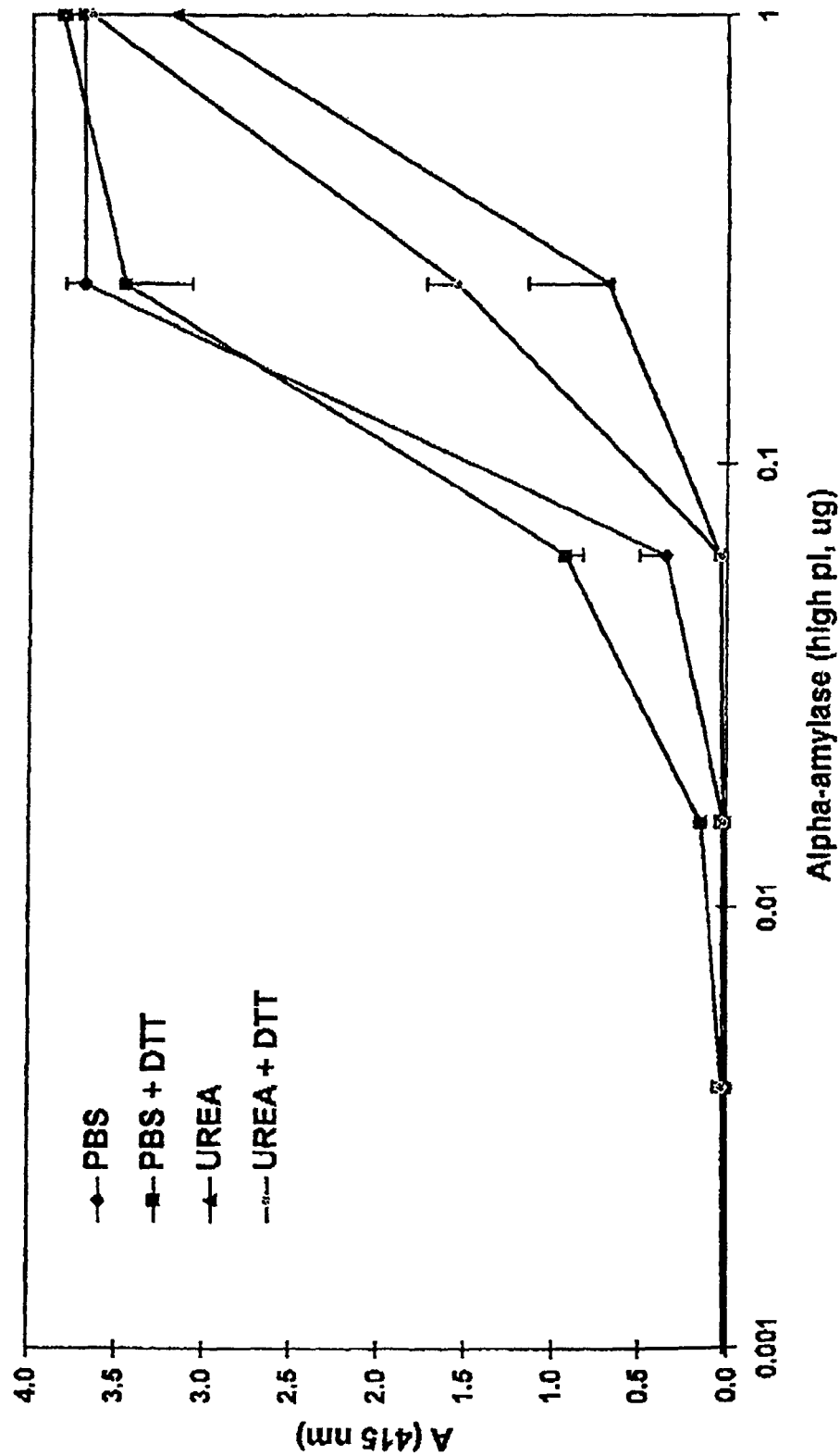
FIG. 4 shows the effect of antigen partial denaturation with urea on detection of high-pI alpha-amylase by three antibodies.
Figure 4B:
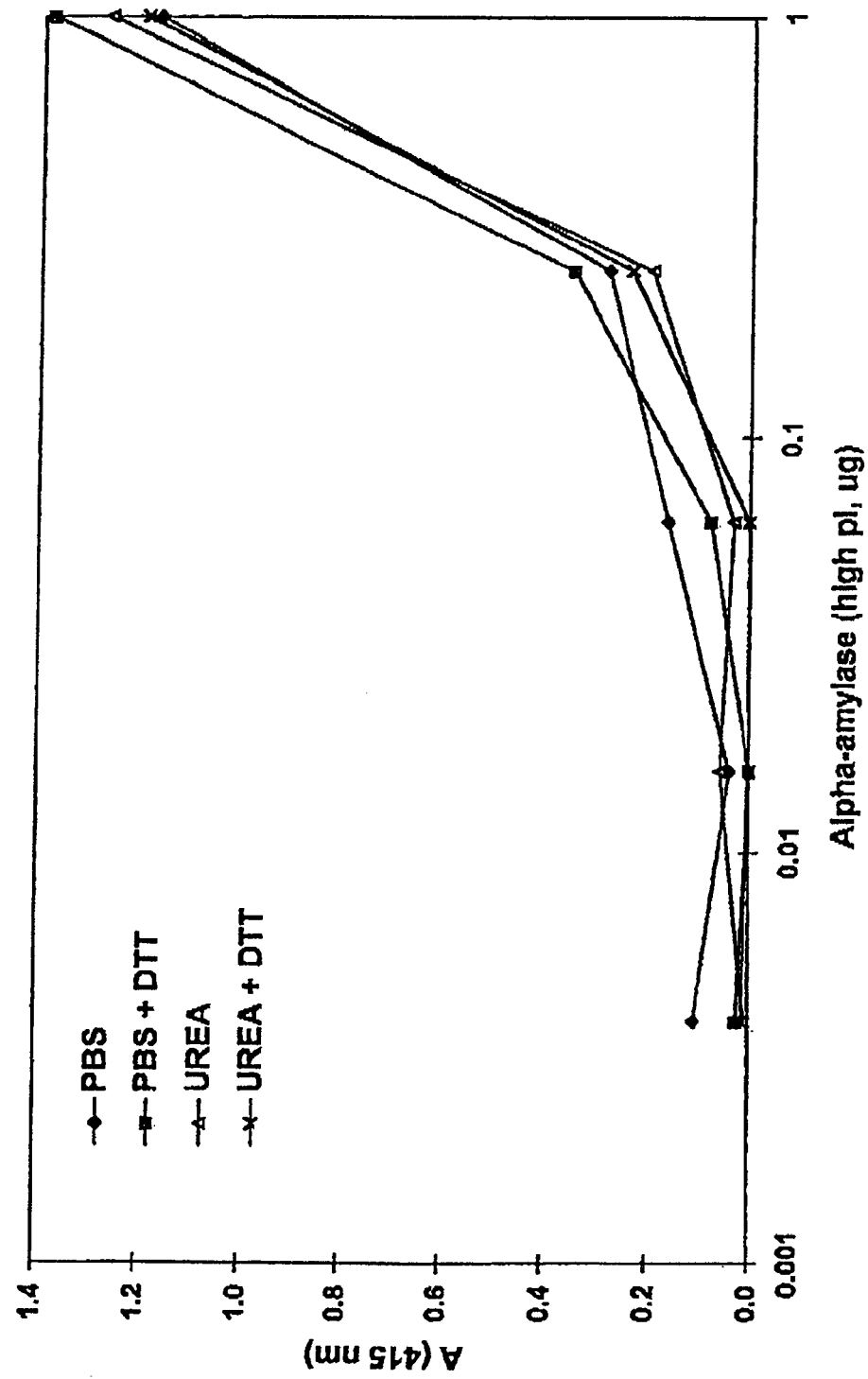
Figure 4C:
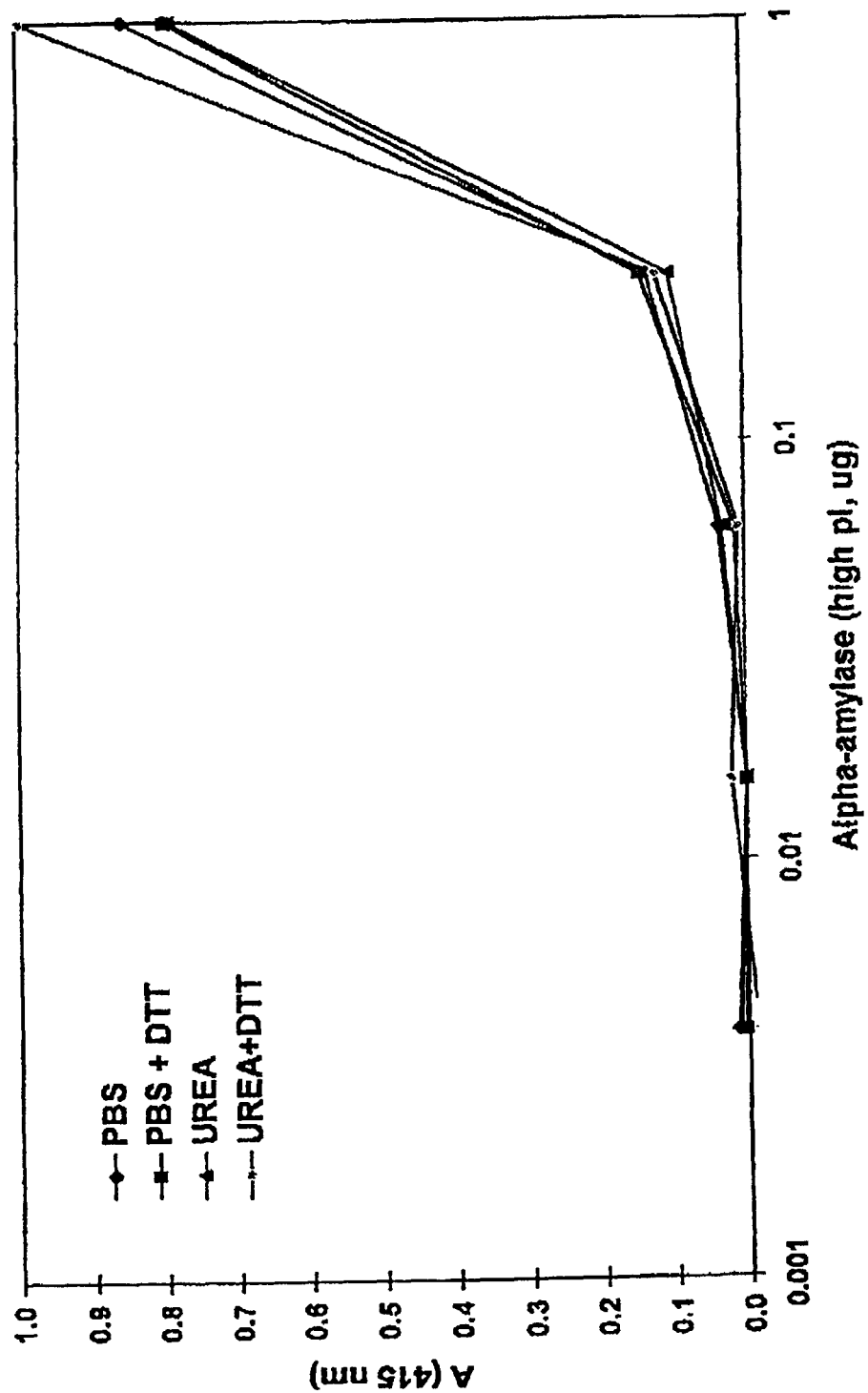

In order to assess whether there was also a difference in the conformational nature between the epitopes recognised by the antibodies which function in the two-site assay and other antibodies to alpha-amylase, effect on antibody binding of partial denaturation with urea of the alpha-amylase antigen were studied. High pI alpha-amylase was dissolved in either: 1. PBS (phosphate-buffered saline, 50 mM sodium phosphate-150 mM NaCl, pH 7.2); 2. PBS—1% (w/v) dithiothreitol; 3. 8 M urea; 4. 8 M urea—1% (v/v) dithiothreitol, at a series of concentrations ranging from 0.01 µg/mL to 10 µg/mL. The antigens were coated onto microwell ELISA plates for 16 hours at 20-23° C. and binding to the PBS-dissolved "native" and treated amylases assessed by indirect ELISA. While each antibody detected native amylase, there was a clear difference in behaviour between different antibodies. The antibodies which functioned in two-site assays (185612 and the polyclonal antisera) bound significantly more poorly to urea-denatured amylase, while the binding of each of the four antibodies that did not function in the two-site assays was unaffected. Reduction with dithiothreitol did not similarly decrease antibody binding. Results with 185612, 15764 and 15689 are shown in FIG. 4. These results provide further evidence that the epitopes recognised by antibodies which functioned in two-site assays had particular and distinct properties and that the conformation of such epitopes was affected by partial denaturation with urea.

Example 3

Rapid Tube Sandwich ELISA for Detection of Alpha-Amylase in Preharvest-Sprouted Wheat Based on the initial performance of the antibodies in the plate sandwich ELISA, rapid tube ELISAs were developed for detection of alpha-amylase. The larger volume of the tubes makes them more suited for field use, since reagents can be added using droppers, and larger reagent volumes can be used, making the assay more acceptable to non-laboratory personnel. Sets of polystyrene test tubes (12 mm diameter×75 mm long) were coated for 16 h at 20° C. with purified capture antibody (5 µg in 500 µL 50 mM sodium carbonate buffer, pH 9.6). Tubes were washed 3 times with PBST, and non-specific binding blocked for 60 min using 1% BSA in PBS. Large batches of tubes could be prepared by freeze drying the antibodies onto the tube surface. The conventional ELISA assay format involving sequential addition of wheat extract and enzyme conjugate, with an intermediate washing step, was simplified to provide an assay protocol involving simultaneous addition of wheat extract and enzyme (with no intermediate washing step). In this assay, antibody HRP conjugates in 1% BSA in PBST were added (50 µL/tube) followed immediately by the addition of 500 µL of undiluted grain extract (prepared in 85 mM NaCl), and incubated for 5-10 min. The initial procedure for extraction of amylase (i.e. blending whole grain in sodium malate buffer) could be simplified by vortex mixing wholemeal flour (ground in the Jupiter mill) for 4 min in malate buffer, and the malate extraction buffer could also be replaced by a simple salt solution (Table II). The use of any of 3 extraction solutions (85 mM or 50 mM NaCl or 50 mM NaCl plus 20 mM $CaCl_2$) provided adequate extraction of enzyme and discrimination between sprouted and sound wheat. Thus an extraction buffer consisting of 85 mM NaCl (which can be made easily under field conditions by dissolving a NaCl tablet in a pre-determined volume of water) was used in subsequent experiments; this may also remove effects of variation in water quality in remote situations. Tubes were washed 3 times with 85 mM NaCl and 500 µL of substrate-chromogen (0.6 mg/mL 3,3',5,5'-tetramethylbenzidine in 0.1 M sodium acetate, pH 5 containing hydrogen peroxide) was added to each tube. The reaction was stopped after 3-5 min by the addition of 250 µL of 1.25 M sulfuric acid. The absorbance was measured at 450 nm using an RPA-1 Rapid Photometric analyser (Source Scientific, Garden City, Calif., USA).

The tube assays were less sensitive than the plate assays with detection limits of approximately 4 ng/mL amylase, probably due to the much shorter incubation periods used. With an initial set of 10 wholemeals, mean ELISA absorbance (colour development) showed a decrease with increasing Falling Number for the tube assay in either format. The results of a comparison in which enzyme was extracted from wholemeal flour in 85 mM NaCl buffer either by intermittent vortex mixing for 4 min, or by wrist-action shaking for 15 sec, showed that hand shaking not only allowed for sufficient extraction of amylase for discrimination between sprouted and sound wheat, it also removed the need for vortex mixing, thus simplifying the tube assay procedure further.

The performance of this assay was tested with several sets of naturally-sprouted grain samples, with Falling Numbers ranging from 62 to 494. This included 56 samples from Western Australia (1995 harvest), 30 samples from the 1995 harvest in New South Wales, Australia (Suneca, Hartog, Sunstate and Janz), 130 samples comprising 8 cultivars (Hartog, Cunningham, Pelsart, Banks, Sunco, Sunstate, Perouse and Janz), from Queensland, Australia (1996 harvest) and 108 samples comprising 6 cultivars (Hartog, Halberd, Sunland, Tincurrin, Matong and Vulcan) from New South Wales, Australia and subjected to controlled wetting. These varieties contained hard and soft wheat types of diverse protein contents (8-15% protein) and end-use types. Falling Numbers for wholemeal (ground with a Falling Number 3100 mill) were determined in duplicate. The analyses were performed with the aim of establishing the relationship between Falling Number and colour development in the ELISA test, as well as establishing whether the relationships noted were substantially independent of the wheat variety analyzed.

The results of these analyses, shown in FIGS. 5A and B, indicated that relative ELISA colour development was strongly (and negatively) correlated with Falling Number for both tube assays. Wheats with Falling Numbers below 350 seconds could be discriminated from sound wheats, with decreasing Falling Numbers producing increasing assay colour.

The results of the ELISA also correlated with alpha-amylase activity measurements, determined using the Ceralpha assay (Megazyme International, Deltagen, Melbourne, Australia), which utilizes p-nitrophenylheptanoside as substrate (McCleary, B. V.; and Sheehan, H. Journal of Cereal Science 6 (1987) 237-251). For the 130 Queensland samples, the correlation between Ceralpha enzyme activity (units/g flour) and Falling Number was r=0.93. Although modifications made to the enzyme assay have increased its sensitivity, it still appeared to be less sensitive than the Falling Number test or the tube ELISA, by failing to clearly discriminate wheat samples with Falling Numbers greater than 250 seconds. Enzymes such as amylases can also be quantified directly by various enzyme assays. The tube ELISA we have developed, showed a strong negative correlation with Falling Number (for 3 diverse sets of wheats) and a positive correlation with the Ceralpha enzyme assay. The ELISA is simple and easy to use, and is reproducible over a wide range of Falling Numbers. Although the tube sandwich ELISA was less sensitive than the plate ELISA, it still had the capacity to detect Falling Numbers below 350 sec (the critical industry cut off point). Above 350 seconds, it has been shown by others that it is difficult to establish close correlations between Falling Number and alpha-amylase activity (Mares, 1989). Analysis of three sets of wheat samples from different environments demonstrated that the relationship between ELISA absorbance and Falling Number had little dependence on wheat variety. The precision of sample analysis using the field ELISA was similar to the precision of the Falling Number test.

Example 4

Immunochromatography Assay for Alpha-Amylase

Immunochromatography (IC), in which bound and unbound components are separated by capillary flow rather than a washing step, potentially provides an even simpler test format that the coated-tube ELISA. Several patents and publications teach the principles of this assay format (Birnbaum, S.; Uden, C.; Magnusson, C. G. M.; Nilsson, S. Analytical Biochemistry 206 (1992) 168-171; Ching, S.; Billing, P.; Gordon, J. U.S. Pat. No. 5,120,643, issued Jun. 9, 1992; Lou, S. C.; Patel, C.; Ching, S.; Gordon, J. Clinical Chemistry 39 (1993) 619-624) and it has been widely applied to the "yes-no" analysis of medical analytes such as urinary human chorionic gonadotrophin analysis in urine for pregnancy testing, and screening for infectious diseases such as malaria. The format has, however, had little application to agricultural analytes.

In the IC format used, a complex of antigen and labelled antibody is allowed to form then migrate by capillary action up a porous test strip. The complex is captured by a band of immobilised antibody on the strip. In the test format used, the wheat grain sample was ground to a fine meal, and 0.5 g meal is shaken with 6 mL of 85 mM NaCl solution in a tube provided. Two drops (60 µL) of the grain extract are added to a sample pad where, if alpha-amylase is present, it binds to an antibody attached to visible (maroon) colloidal gold. A second antibody to alpha-amylase is immobilised as a line across the test strip. After addition of PBS—0.05% Tween 20 wetting agent to the sample pad, the colloidal gold and complexes of colloidal gold and alpha-amylase migrate up the test strip crossing the second antibody line across the test strip. If the sample has a Falling Number below 350 (i.e. contains significant amounts of alpha-amylase), the gold-amylase complex will be captured by the antibody on the membrane and a pink-maroon test line forms. In a negative sample, no test line forms. The card also contains a "control line" of immobilised goat anti-mouse or goat anti-rabbit immunoglobulin antibodies, which provides a positive pink-maroon result in every test.

The different antibody combinations were tested for performance in the IC assay, and only those combinations which functioned in a double-antibody sandwich ELISA (i.e. Mab 185612 and the two polyclonal antibodies) also functioned in the double antibody IC test; antibodies 10413, 15689, 15724 and 15764 did not. Although IC is commonly regarded as a qualitative test format, we found that the intensity of the colour developed in the test line depended upon the concentration of alpha-amylase in the test sample and thus the extent of the weather damage in the sample, such that more colour indicates greater weather damage. Colourless or very pale results occurred when the sample was sound (Falling Number over 350 seconds). The level of weather damage and likely Falling Number for the sample can be determined by analysing some samples of known Falling Number and by comparing test results (FIG. 6). Test results were also reproducible between and within assays (FIG. 7). Results can either be read with respect to standards of known Falling Number, for example on a colour card by using a reflectometer using either white light illumination or light-emitting diode illumination. When manually reading the results of the tests, a 5 min assay time is suitable. It is be possible to further decrease this time in conjunction with a reflectometer.

These assays (in the form of a simple kit) have the potential for on-farm use by individual growers allowing identification of areas of sprouting prior to harvest, thus preventing contamination of sound wheat by wheat that is weather damaged. Currently growers may harvest grain across their whole property, and tests on elevator receival are done on the whole parcel of grain. However, except in very wet harvests, the extent and presence of preharvest sprouting can vary quite markedly between and within fields, being dependant on the rate of drying of the crop after rainfall has occurred (affected by field aspect and drainage), wheat variety sown and time of sowing. Growers usually have an intimate knowledge of the behaviour of different parts of their own property, and if they were able to test the grain from different paddocks and parts of paddocks before harvest, it should be possible to harvest the damaged grain separately from sound grain and avoid the financial losses that result from downgrading the whole crop.

The two-site immunoassays of the present invention enable the simple assessment of the level of alpha-amylase and thus the likely Falling Number of the grain sample. This is of particular advantage since the two-site immunoassays can be applied at mill or silo (elevator) receival of grain or could be used on farms with minimal equipment requirements.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A monoclonal antibody or fragment thereof which specifically or preferentially binds to an epitope on alpha-amylase consisting of one or more of the amino acid sequences selected from the group consisting of SEQ ID NO: 1, SEQ ID NO: 2 and, SEQ ID NO: 3.

2. The monoclonal antibody or fragment thereof according to claim 1 wherein said antibody or fragment specifically binds to an epitope on alpha-amylase consisting of one or more of the amino acid sequences selected from the group consisting of SEQ ID NO: 1, SEQ ID NO: 2 and SEQ ID NO: 3.

3. The monoclonal antibody or fragment thereof according to claim 1 wherein said antibody or fragment specifically or preferentially binds to a conformational epitope on alpha-amylase consisting of one or more of the amino acid sequences selected from the group consisting of SEQ ID NO: 1, SEQ ID NO: 2 and SEQ ID NO: 3.

4. The monoclonal antibody or fragment thereof according to claim 3 wherein said antibody or fragment specifically or preferentially binds to conformational epitope on alpha-amylase consisting of all of the amino acid sequences; SEQ ID NO: 1, SEQ ID NO: 2 and, SEQ ID NO: 3.

5. A kit for performing a two-site immunoassay for the qualitative or quantitative detection of alpha-amylase in a test sample, said kit comprising a container or solid support including a monoclonal antibody or fragment thereof according to claim 1.

6. The kit according to claim 5, further comprising a container including an aqueous extraction agent for extracting alpha-amylase from grain, grain meal or flour.

7. The kit according to claim 6, wherein the extraction agent is aqueous NaCl or $CaCl_2$.

8. The monoclonal antibody or fragment thereof according to claim 1 wherein said antibody or fragment specifically or preferentially binds to an epitope on alpha-amylase consisting of SEQ ID NO: 1.

9. The monoclonal antibody or fragment thereof according to claim 1 wherein said antibody or fragment specifically or preferentially binds to an epitope on alpha-amylase consisting of SEQ ID NO: 2.

10. The monoclonal antibody or fragment thereof according to claim 1 wherein said antibody or fragment specifically or preferentially binds to an epitope on alpha-amylase consisting of SEQ ID NO: 3.

11. The monoclonal antibody or fragment thereof according to claim 2 wherein said antibody or fragment specifically binds to an epitope on alpha-amylase consisting of SEQ ID NO: 1.

12. The monoclonal antibody or fragment thereof according to claim 2 wherein said antibody or fragment specifically binds to an epitope on alpha-amylase consisting of SEQ ID NO: 2.

13. The monoclonal antibody or fragment thereof according to claim 2 wherein said antibody or fragment specifically binds to an epitope on alpha-amylase consisting of SEQ ID NO: 3.

14. The monoclonal antibody or fragment thereof according to claim 3 wherein said antibody or fragment specifically or preferentially binds to a conformational epitope on alpha-amylase consisting of SEQ ID NO: 1.

15. The monoclonal antibody or fragment thereof according to claim 3 wherein said antibody or fragment specifically or preferentially binds to a conformational epitope on alpha-amylase consisting of SEQ ID NO: 2.

16. The monoclonal antibody or fragment thereof according to claim 3 wherein said antibody or fragment specifically or preferentially binds to a conformational epitope on alpha-amylase consisting of SEQ ID NO: 3.

* * * * *

SEQUENCE LISTING

<160> NUMBER OF SEQ ID NOS: 5

<210> SEQ ID NO 1
<211> LENGTH: 15
<212> TYPE: PRT
<213> ORGANISM: Triticum aestivum

```
<400> SEQUENCE: 1

Ile Asp Arg Leu Val Ser Ile Arg Thr Arg Gly Gln Ile His Ser
1               5                  10                  15

<210> SEQ ID NO 2
<211> LENGTH: 10
<212> TYPE: PRT
<213> ORGANISM: Triticum aestivum

<400> SEQUENCE: 2

Cys Arg Asp Asp Arg Pro Tyr Ala Asp Gly
1               5                  10

<210> SEQ ID NO 3
<211> LENGTH: 10
<212> TYPE: PRT
<213> ORGANISM: Triticum aestivum

<400> SEQUENCE: 3

Val Asn Trp Val Asn Lys Val Gly Gly Ser
1               5                  10

<210> SEQ ID NO 4
<211> LENGTH: 425
<212> TYPE: PRT
<213> ORGANISM: Triticum aestivum

<400> SEQUENCE: 4

Met Ala Ser Lys His Leu Ser Leu Phe Leu Val Leu Leu Gly Leu Ser
1               5                  10                  15

Ala Ser Leu Ala Ser Gly Gln Val Leu Phe Gln Gly Phe Asn Trp Glu
                20                  25                  30

Ser Trp Lys His Asn Gly Gly Trp Tyr Asn Phe Leu Met Gly Lys Val
            35                  40                  45

Asp Asp Ile Ala Ala Ala Gly Val Thr His Val Trp Leu Pro Pro Ala
        50                  55                  60

Ser Gln Ser Val Ser Glu Gln Gly Tyr Met Pro Gly Arg Leu Tyr Asp
65                  70                  75                  80

Leu Asp Ala Ser Lys Tyr Gly Asn Lys Ala Gln Leu Lys Ser Leu Ile
                85                  90                  95

Gly Ala Leu His Gly Lys Gly Val Lys Ala Ile Ala Asp Ile Val Ile
            100                 105                 110

Asn His Arg Thr Ala Glu Arg Lys Asp Gly Arg Gly Ile Tyr Cys Ile
        115                 120                 125

Phe Glu Gly Gly Thr Pro Asp Ala Arg Leu Asp Trp Gly Pro His Met
    130                 135                 140

Ile Cys Arg Asp Asp Arg Pro Tyr Ala Asp Gly Thr Gly Asn Pro Asp
145                 150                 155                 160

Thr Gly Ala Asp Phe Gly Ala Ala Pro Asp Ile Asp His Leu Asn Pro
                165                 170                 175

Arg Val Gln Lys Glu Leu Val Glu Leu Leu Asn Trp Leu Arg Thr Asp
            180                 185                 190

Ile Gly Phe Asp Gly Trp Arg Phe Asp Phe Ala Lys Gly Tyr Ser Ala
        195                 200                 205

Asp Val Ala Lys Ile Tyr Val Asp Arg Ser Glu Ala Ser Phe Ala Val
    210                 215                 220

Ala Glu Ile Trp Thr Ser Leu Ala Tyr Gly Gly Asp Gly Lys Pro Asn
225                 230                 235                 240
```

```
Leu Asn Gln Asp Pro His Arg Gln Glu Leu Val Asn Trp Val Asn Lys
                245                 250                 255

Val Gly Gly Ser Gly Pro Gly Thr Thr Phe Asp Phe Thr Thr Lys Gly
                260                 265                 270

Ile Leu Asn Val Ala Val Glu Gly Glu Leu Trp Arg Leu Arg Gly Thr
                275                 280                 285

Asp Gly Lys Ala Pro Gly Met Ile Gly Trp Trp Pro Ala Lys Ala Val
                290                 295                 300

Thr Phe Val Asp Asn His Asp Thr Gly Ser Thr Gln His Met Trp Pro
305                 310                 315                 320

Phe Pro Ser Asp Arg Val Met Gln Gly Tyr Ala Tyr Ile Leu Thr His
                325                 330                 335

Pro Gly Pro Pro Cys Ile Phe Tyr Asp His Phe Phe Asp Trp Gly Leu
                340                 345                 350

Lys Glu Glu Ile Asp Arg Leu Val Ser Ile Arg Thr Arg Gln Gly Ile
                355                 360                 365

His Ser Glu Ser Lys Leu Gln Ile Ile Glu Ala Asp Ala Asp Leu Tyr
                370                 375                 380

Leu Ala Glu Ile Asp Gly Lys Val Ile Val Lys Leu Gly Pro Arg Tyr
385                 390                 395                 400

Asp Val Gly His Leu Ile Pro Gly Gly Leu Lys Val Ala Ala His Gly
                405                 410                 415

Lys Asp Tyr Ala Ile Trp Glu Lys Ile
                420                 425

<210> SEQ ID NO 5
<211> LENGTH: 10
<212> TYPE: PRT
<213> ORGANISM: Triticum aestivum

<400> SEQUENCE: 5

Lys Val Gly Gly Ser Gly Pro Gly Thr Thr
1               5                   10
```